(12) United States Patent
De Man et al.

(10) Patent No.: US 9,125,286 B2
(45) Date of Patent: Sep. 1, 2015

(54) X-RAY DOSE ESTIMATION TECHNIQUE

(71) Applicant: General Electric Company, Schenectady, NY (US)

(72) Inventors: Bruno Kristiaan Bernard De Man, Clifton Park, NY (US); Zhye Yin, Schenectady, NY (US); Xiaoyu Tian, Durham, NC (US)

(73) Assignee: General Electric Company, Niskayuna, NY (US)

( * ) Notice: Subject to any disclaimer, the term of this patent is extended or adjusted under 35 U.S.C. 154(b) by 332 days.

(21) Appl. No.: 13/730,313

(22) Filed: Dec. 28, 2012

(65) Prior Publication Data

US 2014/0185751 A1    Jul. 3, 2014

(51) Int. Cl.
*A61B 6/02* (2006.01)
*H05G 1/28* (2006.01)
*A61N 5/00* (2006.01)
*A61B 6/00* (2006.01)

(52) U.S. Cl.
CPC ........ *H05G 1/28* (2013.01); *A61B 6/542* (2013.01); *A61B 6/4035* (2013.01); *A61B 6/4241* (2013.01)

(58) Field of Classification Search
CPC ........ A61B 6/542; A61B 6/027; A61B 6/032; A61B 6/4028; A61B 6/4241; A61B 6/488; A61B 6/5205; A61B 6/5282; A61N 5/103; A61N 5/1031; A61N 5/1042; A61N 5/1048
USPC ............... 378/65, 62, 143, 165, 5, 51, 53; 250/492.3
See application file for complete search history.

(56) References Cited

U.S. PATENT DOCUMENTS

| 5,422,926 | A  | * | 6/1995  | Smith et al. ............... 378/121 |
| 7,532,705 | B2 | * | 5/2009  | Yin et al. .................. 378/65  |
| 7,734,010 | B2 |   | 6/2010  | Otto et al.                         |
| 2004/0062341 | A1 | * | 4/2004  | Popescu et al. ............ 378/4    |
| 2005/0226363 | A1 | * | 10/2005 | Edie et al. ................. 378/9   |
| 2006/0039533 | A1 | * | 2/2006  | Weil et al. ................. 378/65  |
| 2006/0233295 | A1 | * | 10/2006 | Edic et al. ................. 378/4   |
| 2007/0086569 | A1 | * | 4/2007  | Johnsen ................... 378/65   |
| 2007/0133747 | A1 | * | 6/2007  | Manak et al. ............. 378/62    |
| 2007/0291896 | A1 | * | 12/2007 | Parham et al. ............. 378/37   |
| 2008/0004845 | A1 |   | 1/2008  | Failla et al.                       |

(Continued)

FOREIGN PATENT DOCUMENTS

GB    2479717 A    10/2011
JP    4317665 A    11/1992

OTHER PUBLICATIONS

Alakuijala et al., "SPECT-based Radioimmunotherapy Planning System", Proceedings of the 19th Annual International Conference of the IEEE Engineering in Medicine and Biology Society, pp. 781-784, vol. 2, Nov. 1997.

(Continued)

*Primary Examiner* — David A Vanore
(74) *Attorney, Agent, or Firm* — Robert M. McCarthy

(57) ABSTRACT

Embodiments of the disclosure relate to projection-based volumetric dose estimation for X-ray systems, such as X-ray imaging systems. For example, in one embodiment, an X-ray system is capable of estimating an X-ray dose based on an energy interaction of the X-rays with respective portions of an object. In another embodiment, the X-ray dose estimate may be provided on a per voxel, per region, and/or per organ basis.

19 Claims, 8 Drawing Sheets

(56) References Cited

U.S. PATENT DOCUMENTS

| | | | |
|---|---|---|---|
| 2008/0205717 A1* | 8/2008 | Reeves et al. | 382/128 |
| 2009/0161818 A1* | 6/2009 | Sakurai et al. | 378/15 |
| 2010/0119033 A1* | 5/2010 | Li et al. | 378/5 |
| 2011/0051893 A1 | 3/2011 | McNutt et al. | |
| 2011/0122997 A1* | 5/2011 | Lu et al. | 378/65 |
| 2012/0029862 A1* | 2/2012 | Scholz et al. | 702/127 |
| 2012/0041685 A1 | 2/2012 | Ding et al. | |
| 2013/0156149 A1* | 6/2013 | Kohara | 378/4 |
| 2014/0105356 A1* | 4/2014 | Yin et al. | 378/62 |
| 2014/0177794 A1* | 6/2014 | De Man et al. | 378/62 |
| 2014/0185751 A1* | 7/2014 | De Man et al. | 378/51 |
| 2014/0233706 A1* | 8/2014 | Weigand | 378/143 |

OTHER PUBLICATIONS

Zhang et al., "A Novel Applicator System for HDR Treatment of Endometrial and Cervical Cancer", International Journal of Radiation Oncology, pp. S810-S811, vol. 78, Issue 3, Nov. 1, 2010.

Badal et al., "SU-E-I-68: Fast and Accurate Estimation of Organ Doses in Medical Imaging Using a GPU-Accelerated Monte Carlo Simulation Code" The International Journal of Medical Physics Research and Practice, vol. 38, Issue 6, 2011.

Chen et al., "Fast on-site Monte Carlo Tool for dose calculations in CT Applications", The International Journal of Medical Physics Research and Practice, pp. 2985-2997, vol. 38, Issue 6, May 10, 2012.

* cited by examiner

X-RAY DOSE ESTIMATION TECHNIQUE

BACKGROUND

The subject matter disclosed herein relates to X-ray imaging techniques and, more particularly, techniques for estimating a received X-ray dose per volume.

In non-invasive imaging systems, X-ray tubes are used in various X-ray systems and computed tomography (CT) systems as a source of X-ray radiation. The radiation is emitted in response to control signals during an examination or imaging sequence. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce X-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals may then be processed to generate an image that may be displayed for review. In other systems, such as systems for oncological radiation treatment, a source of X-rays may be used to direct ionizing radiation toward a target tissue. Regardless of the type of X-ray system used, it may be beneficial to limit X-ray exposure during individual imaging or treatment events. Accordingly, an X-ray device may use settings that achieve appropriate imaging or therapy results at a lowest possible X-ray exposure.

BRIEF DESCRIPTION

In one embodiment, a method is provided that uses a processor and that includes the steps of: receiving information generated by an X-ray detector related to detected X-rays of an X-ray beam that have passed through an object; estimating a first energy interaction with a first portion of the object based on an intensity profile of the detected X-rays of the X-ray beam; estimating a remaining energy in the X-ray beam after passing through the first portion of the object; estimating a second energy interaction with a second portion of the object adjacent to the first portion of the object, wherein the X-ray beam passes through the first portion before the second portion, based on the remaining energy; determining a first estimated dose value for the first portion based at least in part on the first energy interaction and the mass of the first portion of the object; and determining a second estimated dose value for the second portion based at least in part on the second energy interaction and the mass of the second portion of the object.

In another embodiment, an X-ray system is provided that includes an X-ray source configured to generate an X-ray beam through a plurality of projection lines and a detector configured to detect X-rays of the X-ray beam that pass through an object for each respective projection line. The system also includes a processor coupled to the detector and configured to receive information generated by the detector related to the detected X-rays. The processor is configured to execute instructions for: dividing the object into a plurality of respective volumes; determining an intensity profile of the detected X-rays that pass through each respective volume for each respective projection line; determining an attenuation profile of the detected X-rays that pass through each respective volume for each respective projection line; estimating an energy interaction for each respective volume based on the intensity profile for each respective projection line; estimating a mass for each respective volume of the object based on at least one attenuation profile; and determining an estimated dose value for the object based at least in part on the energy interaction with each respective volume of the object for each respective projection line and the mass of each respective volume of the object.

In another embodiment, an X-ray system includes a processor configured to receive information generated by an X-ray detector related to X-rays that have passed through an individual volume of an object, wherein the processor is configured to execute instructions for: determining an intensity profile of the detected X-rays that pass through the volume of the object; estimating an energy interaction with the volume of the object based on the intensity profile; and determining a remaining energy in the X-ray beam after the energy interaction.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
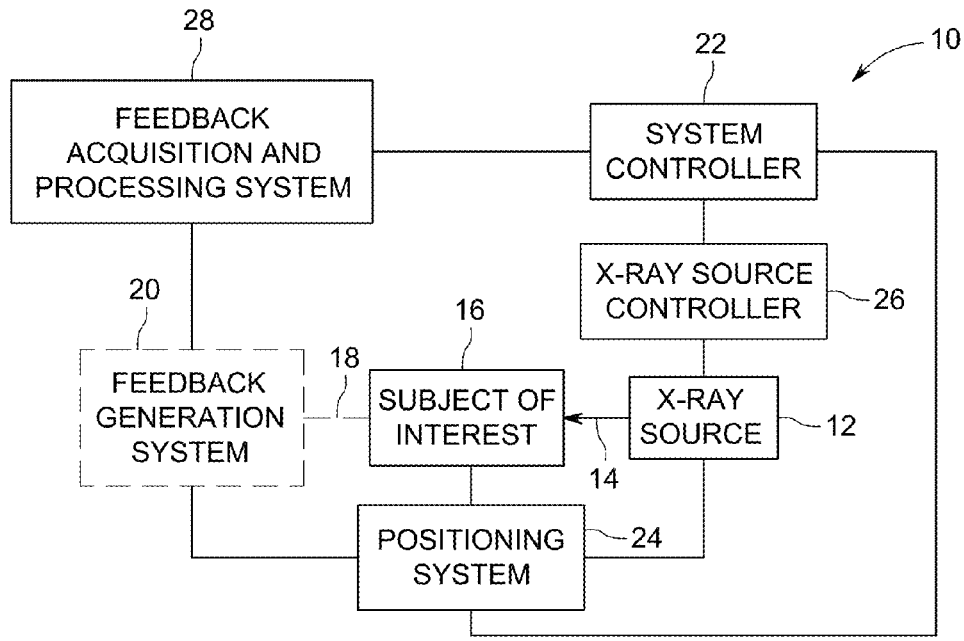
FIG. 1 is a block diagram illustrating an embodiment of a system that uses an X-ray source capable of emitting X-rays that may be used in conjunction with the dose estimation techniques according to an embodiment of the present disclosure.

While X-ray imaging and/or treatment devices may be configured to facilitate X-ray exposure at a sufficiently high dose to achieve desired results, operators may also wish to limit X-ray exposure for patients and/or X-ray technicians. The present disclosure provides X-ray dose estimation techniques that may be used to estimate X-ray doses of a patient (or exposed object) from particular settings used in conjunction with X-ray devices. As provided herein, the X-ray dose estimation approach may be prospective or retrospective and may be used to design and to assess dose-saving or dose-limiting features and protocols.

The X-ray dose reconstruction approaches provided herein may be used to provide dose estimation per voxel, per region, or per organ for a given imaged object. Further, the disclosed implementations improve upon dose estimation techniques that assume that all views irradiate the same volume. In particular, the approach involves reconstructing a total volume or organ dose, starting from the estimated interaction energy in each projection line or view. The techniques involve backprojection operations that keep track of the remaining energy in a given projection line as the x-ray beam penetrates through the patient. Provided herein are implementations that allow a distance-driven framework to be applied to other techniques for does estimation footprints, pixel- or voxel-driven techniques, blob-based techniques and other back-projection techniques.

In particular embodiments, the disclosed techniques may be used to assess the dose variation across a given object, such as a patient organ. For example, different portions of an organ may receive different doses depending on their orientation and position relative to an X-ray source as well the anatomical variation within the organ (e.g., soft tissue areas vs. bone areas). Further, the edges of a particular organ may behave differently than the interior of the organ. By providing a volumetric assessment of an X-ray dose, a more accurate assessment of the total dose for a given object may be achieved. Further, the volumetric-based techniques may also facilitate a more accurate assessment of a projected dose variation or maximum within a particular organ. For radiation-sensitive organs, a maximum dose may be used as a threshold rather than a total dose across the organ.

The techniques disclosed herein provide the benefit of projecting or estimating an X-ray dose for a given treatment. Further, the X-ray dose estimation may incorporate information from relatively lower X-ray dose preparatory scans (e.g., scout or reconstructed images from ultra-low dose acquisition scans) that occur before a full imaging scan. Such preparatory scans may involve a limited number of views or may involve multiple views of the patient. For example, information from a preparatory or scout scan may be used to determine an intensity profile for the scanned object. Based on the intensity profile of the detected X-rays and an estimate of the mass of the scanned object, a dose estimate may be determined. The dose estimate based on a preparatory scan may be further used (e.g., fitted to a line or used as a variable in a transfer function) in conjunction with the desired imaging or treatment energy settings to determine the projected dose to the object during imaging and/or treatment. In this manner, the estimated X-ray dose may be assessed on a per patient and per treatment basis. If the estimated dose is outside a desired range or threshold, the settings of the device may be changed, e.g., manually or automatically, until a desired estimated dose is achieved. In yet another embodiment, the dose estimation techniques may be used to retroactively determine the dose received by the scanned object. Such techniques may be useful for tracking or reporting total X-ray exposure of a patient or for tracking performance of a particular X-ray device.

Figure 2:
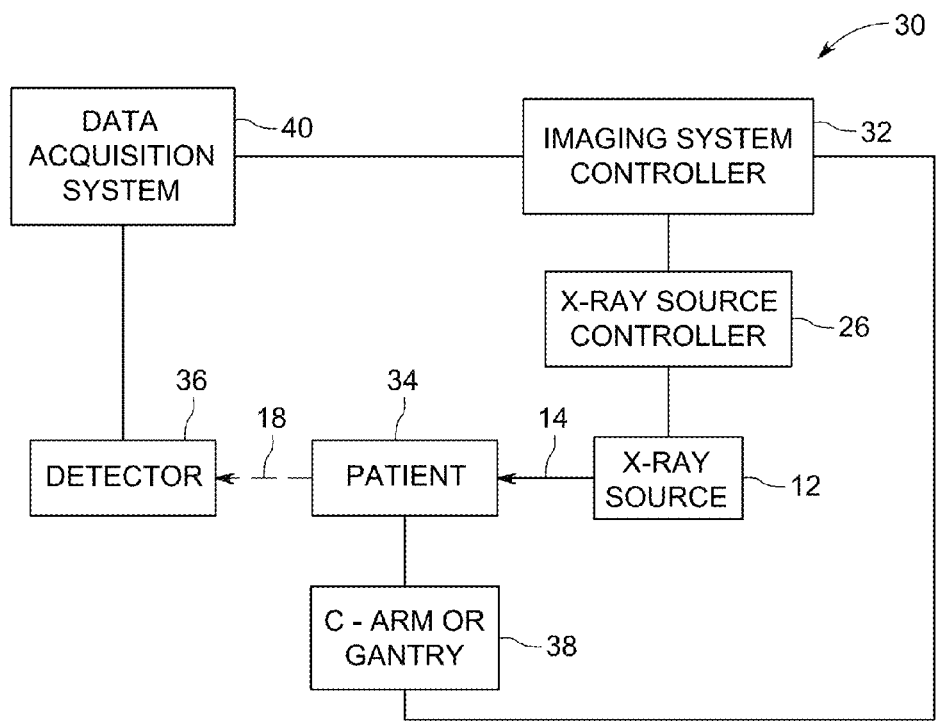
FIG. 2 is a block diagram illustrating an embodiment of an X-ray imaging system that uses an X-ray source capable of emitting X-rays that may be used in conjunction with the dose estimation techniques according to an embodiment of the present disclosure.

The approaches described herein may be used in the appropriate context, which may include non-invasive imaging, surgical navigation, radiation treatment, and so on. Accordingly, FIGS. 1 and 2 provide non-limiting examples of systems that may include control circuitry and control logic in accordance with the present approaches. Specifically, FIG. 1 is a block diagram illustrating a general system 10 that uses an X-ray radiation source 12 for performing a quality control, security, medical imaging, surgical, and/or treatment procedure. The X-ray radiation source 12 may include one or more X-ray tubes each having features for producing X-ray radiation from more than one perspective and/or of more than one energy in a controlled manner as noted above. The X-ray source 12 therefore produces one or more streams of X-ray radiation 14 that are directed towards a subject of interest 16. The subject of interest may be baggage, cargo, an article of manufacture, a tissue of interest, and/or a patient. The X-ray radiation 14 is directed towards the subject of interest 16, where the X-ray radiation is attenuated to produce a beam of attenuated X-rays 18. The beam of attenuated X-rays 18 is captured by a feedback generation system 20 to produce signals representative of an image, or other information that may be useful for performing the procedure. Again, the data produced at the feedback generation system 20 may include data produced from receiving X-rays from a variety of positions and/or energies from each X-ray tube of the source 12.

A system controller 22 commands operation of the system 10 to execute examination, treatment and/or calibration protocols and to process the feedback. With respect to the X-ray source 12, the system controller 22 furnishes power, focal spot location, focal spot size, control signals and so forth, for the X-ray examination sequences. For example, the system controller 22 may furnish focal spot sizes and/or locations for X-ray emissions by the X-ray source 12. Additionally, in some embodiments, the feedback generation system 20 is coupled to the system controller 22, which commands acquisition of the feedback. The system controller 22 may include signal processing circuitry and associated memory circuitry. In such embodiments, the memory circuitry may store programs, routines, and/or encoded algorithms executed by the system controller 22 to operate the system 10, including one or more features of the X-ray source 12, and to process the feedback acquired by the generation system 20. In one embodiment, the system controller 22 may be implemented as all or part of a processor-based system such as a general purpose or application-specific computer system.

The source 12 may be controlled by an X-ray source controller 26 contained within or otherwise connected to the system controller 22. The X-ray source controller 26 is configured to provide power and timing signals to the source 12. In some embodiments the X-ray source controller 26 may be configured to selectively activate the source 12 such that tubes or emitters at different locations within the system 10 may be operated in synchrony with one another or independent of one another. The X-ray source 12 is positioned about the subject of interest 16 by the positioning system 24. The positioning system 24, as illustrated, may be connected to the feedback generation system 20. The positioning system 24 may displace either or both of the X-ray source 12 and the feedback generation system 20 to allow the source 12 to image or treat the subject of interest 16 from a variety of positions. As an example, in a radiation treatment procedure, the positioning system 24 may substantially continuously displace the X-ray source 12 about the subject of interest 16, which may be a tissue of interest, while varying the energy of the X-ray radiation 14 emitted toward the tissue of interest. In this way, the tissue of interest is provided with a substantially continuous flux of X-ray radiation while X-ray exposure to outlying tissues is minimized.

Moreover, while some systems may not produce diagnostic images of the patient, the feedback generation system 20 may generate data relating to the position of the X-ray source 12 or other features, such as a surgical tool, relative to the tissue of interest, for example as an image and/or map. Such data may enable a clinician or other healthcare provider to ensure that the X-ray radiation 14 and/or the surgical tool is properly located with respect to the tissue of interest. The feedback generation system 20 may include a detector, such as a diode array, or a system that monitors the position of the source 12 and/or surgical tool relative to the subject of interest 16. Indeed, in certain embodiments, the feedback generation system 20 may include a detector and position-monitoring features that also provide feedback to the positioning system 24 either directly or indirectly.

To provide feedback to features of the system 10 that are not directly connected to or associated with the feedback generation system 20, the feedback generation system 20 provides data signals to a feedback acquisition and processing system 28. The feedback acquisition and processing system 28 may include circuitry for receiving feedback from the feedback generation system 20, as well as processing circuitry for manipulating the received data. For example, the processing circuitry may include signal converters (e.g., A/D converters), device drivers, processing chips, memory, and so on. In some embodiments, the feedback acquisition and processing system 28 converts analog signals received from the feedback generation system 20 into digital signals that can be further processed by one or more processing circuits (e.g., a computer-based processor) of the system controller 22.

One embodiment of system 10 is illustrated in FIG. 2, which is a block diagram of an embodiment of an X-ray imaging system 30, such as a computed tomography (CT) or other radiographic imaging system. The system 30 includes an imaging system controller 32 for acquiring and processing estimation data. The imaging system controller 32 also includes or is otherwise operatively connected to the X-ray source controller 26, which operates as described above. The X-ray source controller 26 may also be operatively connected to a plurality of magnetic coils that are disposed proximate an X-ray tube of the source 12.

Generally, the system 30 situates a patient 34 such that the X-ray beam 14 produced by the source 12 is attenuated by the patient 34 (e.g., various anatomies of interest) to produce the attenuated X-rays 18 that have passed through the patient 34, which may be received by a detector 36, such as a digital detector. In certain embodiments, the patient 34 may be situated in this manner using a patient table combined with a C-arm or gantry 38, which is controllably connected to the imaging system controller 32. Generally, the imaging system controller 32 may synchronize certain imaging sequence parameters, such as emissions from the source 12 with rotation rates of the source 12 and detector 36 about the gantry.

The data that is generated at the detector 36 upon receiving the attenuated X-rays 18 is provided, as above, to processing features such as the illustrated data acquisition system (DAS) 40. The DAS 40 generally converts the data received from the detector 36 into a signal that can be processed at the imaging system controller 32 (or other computer based processor). As an example, the detector 36 may generate analog data signals upon receiving the attenuated X-rays 18, and the DAS 40 may convert the analog data signals to digital data signals for processing at the imaging system controller 32. The data may be used to generate one or more volumetric images of various anatomies within the patient 34. Further, the data may be used to implement one or more embodiments of the disclosed techniques for X-ray dose estimation.

As noted, the above systems are examples of systems that may be used in conjunction with the X-ray dose estimation methods disclosed herein. Further, the methods disclosed herein may include various steps or actions represented by blocks in the flow diagrams. It should be noted that the methods may be performed as an automated procedure by a system, such as system 10 or system 30. Further, certain steps or portions of the method may be performed by separate devices or may involve operator actions or input.

Figures 3, 4:
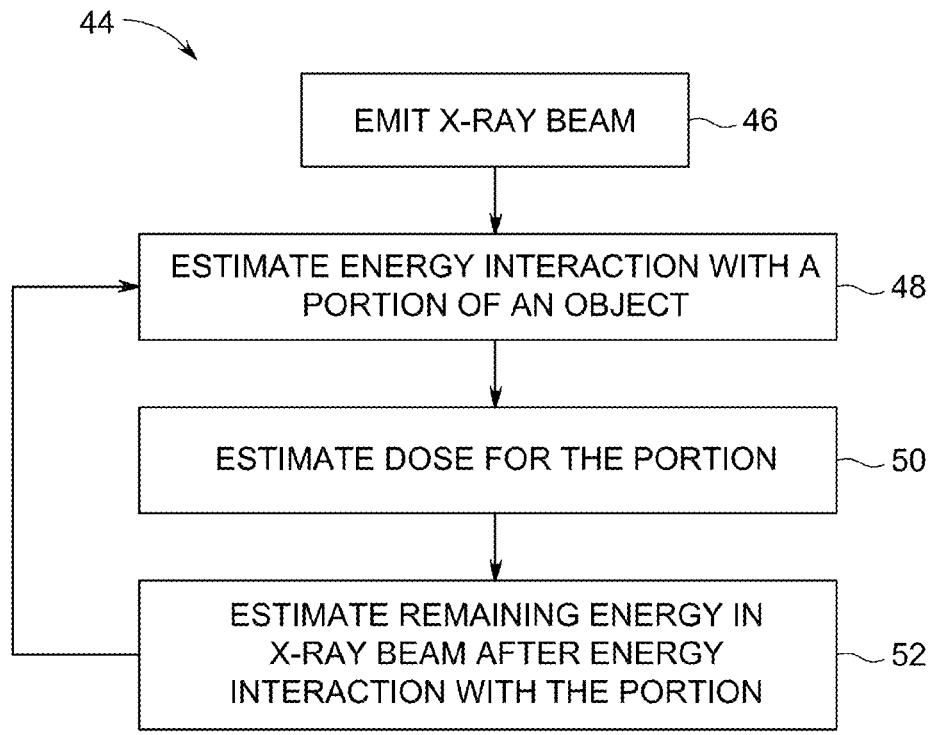
FIG. 3 is a flow diagram of a dose estimation technique according to an embodiment of the present disclosure.
FIG. 4 is a flow diagram of a dose estimation technique according to an embodiment of the present disclosure.

FIG. 3 is a flow diagram of a method 44 that may be used in conjunction with the disclosed embodiments. At block 46, an X-ray beam 18 is emitted from an X-ray source 12 through a desired object, such as a patient 34. The emitted X-ray beam 18 may represent a single projection line through the object. As the X-ray beam 18 passes through the object, it interacts first with a portion that is closest to the source 12. At block 48, the method 44 estimates the energy interaction with only a portion of the object. For example, the portion may represent a predefined volume, such as a voxel. Further, in certain embodiments, the object is divided into volumes of generally equal size. The size may be determined by the system (e.g., system 10 or system 30) or by the resolution specification determined by the application needs.

Based on the energy interaction, the received dose for the portion may be estimated at block 50. After the X-ray beam 18 passes through the first portion, the energy is attenuated such that adjacent portions receive less energy. Accordingly, the remaining energy in the X-ray beam 18 is estimated after interaction with a particular portion at block 52. After estimating the remaining energy, the method 44 may return to block 48 to continue determining dose values for adjacent volumes conjunction with estimated mass of given volume. For example, the method 44 may start with determining an estimated dose for the closest or first portion relative to the X-ray source 12 and then may subsequently determine the estimated dose for all adjacent portions (i.e., adjacent to the first portion) to account for lower-energy X-ray beam. In turn, the next layer of volumes may be analyzed to determine an estimated dose and so on. In this manner, the estimated dose for individual portions may be determined for a given object. In one embodiment, areas of the object closer to the X-ray source are estimated to receive higher doses relative to areas farther away from the X-ray source.

Once the estimated dose values for a plurality of portions or volumes are determined, the total dose of the object may be determined, as shown in FIG. 4, which illustrates a flow diagram for a method 56. At block 58, the estimated dose values for the portions in the object are acquired. Based on the estimated doses for each of the plurality of portions, the dose of the object may be determined at block 60. The dose for the object may be provided to an operator in any suitable format. For example, the estimated dose information may be provided as an index or numerical indicator, e.g., a total dose for an object, an average dose for the object, a maximum estimated dose within the object, etc. In addition, the estimated dose information may be provided as an overlay and/or in addition to X-ray image data. In one embodiment, an estimated dose map may be provided on the image with dose information provided at corresponding locations on the image of the scanned object. Further, the disclosed techniques may be used in conjunction with image segmentation techniques to determine the edges of a particular organ.

Certain embodiments of the disclosure provide techniques for calculating X-ray dose volumetrically, e.g., per voxel or volume element that is relatively computationally efficient and that is patient-specific. In particular, the techniques example the interaction energy, $E_{int}$, or the amount of energy that was removed from the primary X-ray beam prior to reaching the detector, by a combination of the physical attenuation processes in the patient, such as photo-electric absorption or Compton scatter or in the case of high energies also pair formation. This quantity can directly be calculated from X-ray dose estimation techniques, by subtracting the actual patient or object scan from the air scan, as disclosed herein. In the case of an energy-integrating detector, the measured signal is the total energy that penetrates through the patient and is absorbed by the detector. In the case of a photon-counting detector, an energy-weighted sum over all energy bins yields a similar estimate. Integrating across all detector channels results in the total interaction energy for a particular x-ray projection measurement or view.

The absorbed dose is absorbed energy per unit mass. The interaction energy is correlated to the absorbed energy. Both quantities may differ in that the first includes scattered energy and the latter does not. However, for certain scan parameters, there exists a monotonic relationship between absorbed energy and interaction energy.

The mass of a given slice or volume may be approximated by the sum over all channels of all line integrals of the linear attenuation coefficient (which is approximately proportional to the mass density). This is also an approximation in fan-beam or cone-beam geometries due to the geometric magnification, but averaging the mass over a number of view angles may yield a better approximation In summary, the dose for a given volume is estimated as:

$$\text{Dose} = \Sigma_{views}\{f(\Sigma_{channels}(I_{air}-I_{patient}))/ \Sigma_{views}[\Sigma_{channels}(-\log(I_{patient}/I_{air}))]/\text{number of views}\} \quad (1)$$

where $I_{air}$ is the air scan intensity profile and $I_{patient}$ is the patient or object scan intensity profile. Additional additive, multiplicative, or convolutional empirical correction factors can be included to better approximate the true dose. An effective dose may be computed by multiplying the above estimate by patient- and anatomy-dependent weighting factors. Alternatively, in the computation of the effective dose the average mass estimate for the irradiated volume may be substituted by a mass estimate of the entire patient.

The disclosed techniques provide dose estimated for given individual volumes. For example, the volumes may be present by the imaging system 10 and may be a voxel or may be a volume associated with a desired unit of measure. Further, the volume/s may be associated with a particular organ or feature of an imaged object. Accordingly, the imaged object may be considered as a three-dimensional array of individual volumes FIG. 3 illustrates a schematic diagram of single x-ray beam with intensity $I_0$ as it penetrates the first row or slab in the image with Interaction attenuation coefficient $\mu$ and thickness d and incidence angle $\theta$. The energy interacted with the first row in the image is computed as:

$$E_1 = I_0 * (1-\exp(-\mu*d*\cos\theta)), \quad (2)$$

and the remaining intensity as the beam enters the next row is computed as:

$$I_1 = I_0 * \exp(-\mu*d*\cos\theta). \quad (3)$$

Figure 5:
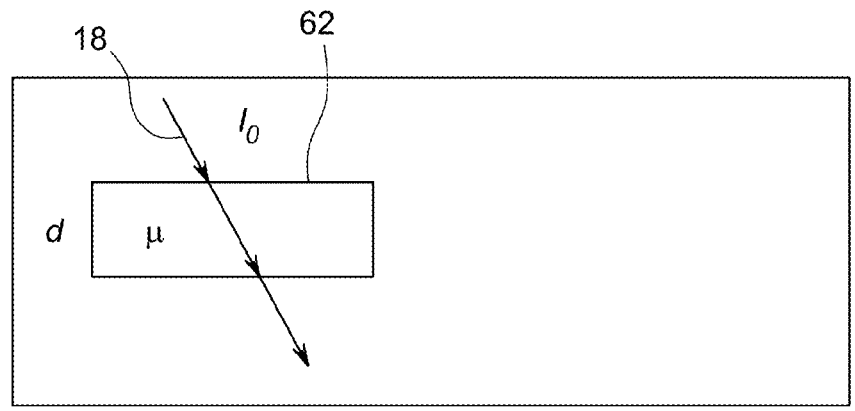
FIG. 5 is a schematic diagram of an X-ray beam interacting with a volume with attenuation coefficient μ and thickness d.
Figure 6:
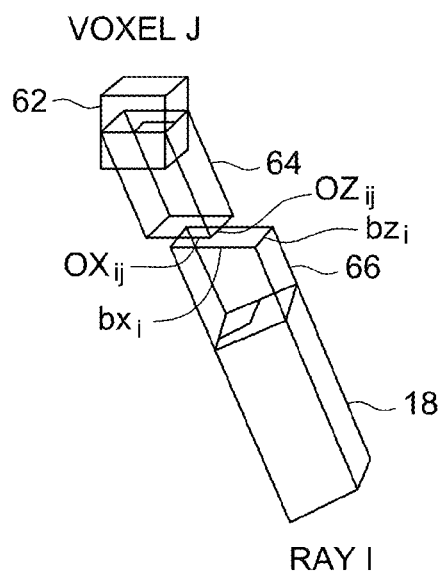
FIG. 6 is a schematic diagram of overlap coefficients for a voxel and an X-ray beam.

In certain embodiments, a given voxel (or volume) will only absorb part of the energy $E_1$, proportional to its footprint in the beam compared to the footprint of the entire beam. FIG. 5 is a schematic diagram of overlap coefficients for voxel j and ray i. The distance-driven overlap kernel may be used to compute this relative footprint, so the interaction energy for voxel j from beam i is computed as:

$$E_{1j} = (ox_{ji}*oz_{ji})/(bx_i*bz_i) * I_0 * (1-\exp(-\mu_j*d*\cos\theta)), \quad (4)$$

where $ox_{ji}$ and $oz_{ji}$ are the overlap coefficients between voxel j and beam i in the x and z direction respectively, and $bx_i$ and $bz_i$ are the beam widths of beam i in the x and z direction respectively. The linear attenuation coefficient $\mu$ is obtained from a CT reconstruction (such as based on filtered back-projection or iterative reconstruction).

In general, the interaction energy and dose can be tracked similarly when going from slab n to slab n+1.

$$E_{n+1,j} = (ox_{ji}*oz_{ji})/(bx_i*bz_i) * I_n * (1-\exp(-\mu_j*d*\cos\theta)),$$

$$I_{n+1} = I_n * \exp(-\mu_{average}*d*\cos\theta). \quad (5)$$

The sum of all interaction energies across the slabs equals the per-cell interaction energy from a sinogram-based method (such as those disclosed in U.S. patent application Ser. No. 13/649,942, filed on Oct. 11, 2012, and entitled "X-Ray Dose Estimation Technique" to Zhye Yin et al., the disclosure of which is incorporated by reference herein in its entirety for all purposes), because $$[1-\exp(-p_1)]+[\exp(-p_1)(1-\exp(-p_2))]+[\exp(-p_1-p_2)(1-\exp(-p_3))]=1-\exp(-p_1-p_2-p_3-\ldots) \quad (6)$$

Where $p_i$ is attenuation at $i^{th}$ row of image. For projections that are more vertical, the beam may be tracked from row to row (in y) (from xz-slab to xz-slab). For projections that are more horizontal, the same procedure is followed from column to column (or from yz-slab to yz-slab), and the index x is replaced by y.

A conversion from interaction energy to dose may be made by correcting for scatter effect. This could be performed uniformly across the entire volume, or may be performed in a more complex voxel-dependent fashion (for example more photons are likely to scatter out of the patient for interactions near the edge). The mass in each voxel can be estimated from $\mu$, either using a simple scale factor, or from a lookup table to normalize by mass.

The process of dose reconstruction may not involve the same spatial resolution as for diagnostic imaging. Hence, the procedure may be performed on a coarse voxel scale and/or coarse sinogram pixels depending on the clinical needs, i.e. region dose or organ dose.

If the CT scan is an energy-sensitive CT scan, more accurate interactions can be computed by distinguishing between Compton scatter and photo-electric absorption. Scattered energy may then be treated separately from absorbed energy. Also, mass estimates can be made very accurately from the photo-electric and Compton scatter components of each voxel.

If a good estimate of the spectrum is available, the polychromatic nature of the x-rays can be taken into account. The spectrum is divided in a number of energy bins, and the above procedure is repeated for each energy bin. The total dose is the sum of the doses at each energy.

Figure 7:
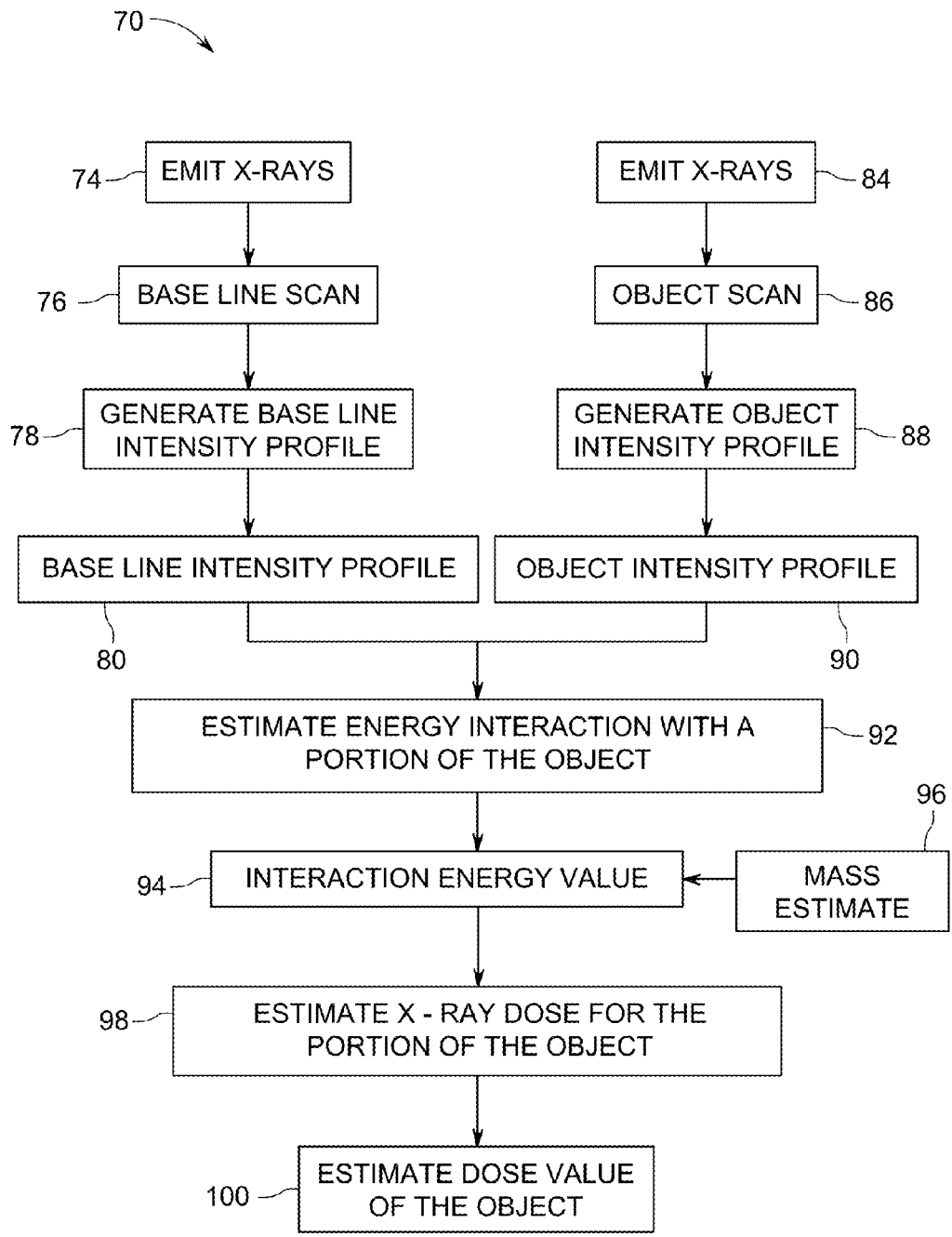
FIG. 7 is a flow diagram of a dose estimation technique according to an embodiment of the present disclosure.

In certain embodiments, the X-ray dose estimation technique provided herein may incorporate dose estimation techniques such as those provided in U.S. patent application Ser. No. 13/649,942. To that end, FIG. 7 is a process flow diagram illustrating a method 70 of estimating an X-ray dose in accordance with some embodiments. According to the embodiment illustrated, the method 70 begins with emitting X-rays from an X-ray source 12 at block 74 to generate an air scan or baseline scan 76 at block 74. In one embodiment, the baseline scan 76 represents detection of X-rays when a scanned patient or object is not in the field of view (FOV). The baseline scanning step at block 74 may be performed periodically (e.g., prior to every dose estimation) or may be performed as a calibration step for the system (e.g., system 30) or the X-ray source 12 and the detector 36. For example, the calibration may be performed as part of the routine scan procedure and the baseline scan results may be stored in a memory associated with the system 30 (e.g., a mass storage device associated with the DAS 40). The baseline scan results may include data from a detector that may be further processed and/or analyzed as provided herein. For example, the baseline scan is used (block 68) to generate a baseline intensity profile 80.

The patient or object of interest is scanned at block 84 to generate an object scan 86. The object scan 86 in turn may be used (block 88) to generate an object intensity profile 90. The intensity profiles 80 and 90 may be provided as raw data or may be provided as a plot of the energy over a range of channels or positions. For example, the intensity may be expressed in any appropriate absolute intensity unit or as an arbitrary relative unit. Further, the intensity may be expressed with regard to position of the scanned object. The position may be expressed as a measured position within the field of view, a distance from a center of the field of view, a pixel position, or as a position associated with a particular channel. The baseline intensity profile 80 and the object intensity profile 90 are used to estimate the energy interaction with the object (block 92) to generate an interaction energy value 94 for a portion or volume of the object. The interaction energy value 94 and a mass or size estimate 96 for the object are used to estimate an X-ray dose (block 98) to generate an estimated dose value 100 for a particular X-ray setting for a particular portion.

The estimated dose value 100 may in turn be displayed or otherwise provided as an indication to an operator of an associated system (e.g., system 10 or system 30) The estimated dose value 100 may be compared manually or automatically to a range or threshold to determine if the estimated dose value 100 is appropriate for the desired application. Further, the estimated dose value 100 may be used to automatically select settings for the associated system, including imaging or treatment settings.

For example, the intensity profiles 80 and 90 generated by a patient and object scan, respectively, are shown in FIG. 5, which shows side-by-side schematic views of an example of a baseline scan 102 and an object scan 104. After photons from an X-ray tube first pass through beam shaper 106, which may include components such as a bowtie filter, collimator, and so forth, they are absorbed, scattered by, or pass through the object, shown as patient 34. The photons that do not get absorbed are detected at the detector 36. In the baseline scan case, most of the photons pass through to the detector 36. With the exception of any scattered photons, the lost intensity energy in the object scan is through energy absorption by the object or the energy interaction with the object. The difference between the baseline intensity profile 80 and the object intensity profile 90 represents the lost intensity due to the patient 34 and, thus, may be translated into the energy interacted with the patient 34.

Figure 9:
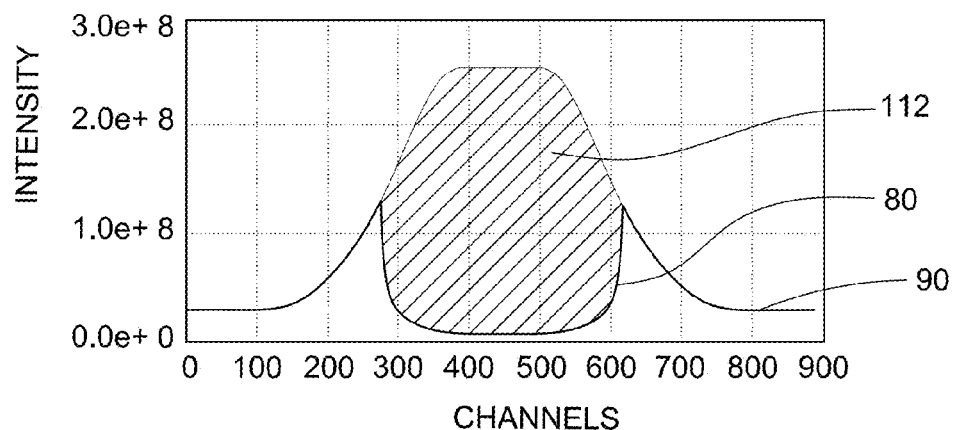
FIG. 9 is an example of a combined baseline intensity profile and object intensity profile that may be used to estimate an interaction energy in conjunction with the dose estimation techniques according to an embodiment of the present disclosure.

The baseline intensity profile 80 and the object intensity profile 90 may be used in conjunction with one another to determine an energy interaction with the object or patient 34. As shown in FIG. 9, an example of a combined plot 110 shows a shaded area 112 between the baseline intensity profile 80 and the object intensity profile 90 when aligned along the x-axis 120 and where the y-axis represents a common relative intensity scale. Here, the shaded area between the two curves represents an estimate of the energy interaction with the object or patient 34. In certain embodiments, the baseline scan 76 and the object scan 86 may include data from a single view (i.e., only one view) or may involve multiple views. Fewer views may be associated with relatively faster analysis. That is, the X-ray source 12 and patient 34 may move relative to one another so that multiple projections may be acquired, such as at different radial views. In such embodiments, the estimates of interaction energy determined via intensity profiles 80 and 90 from individual views may be combined or averaged. In other embodiments, an estimated dose may be determined on a per view basis.

Figure 8:
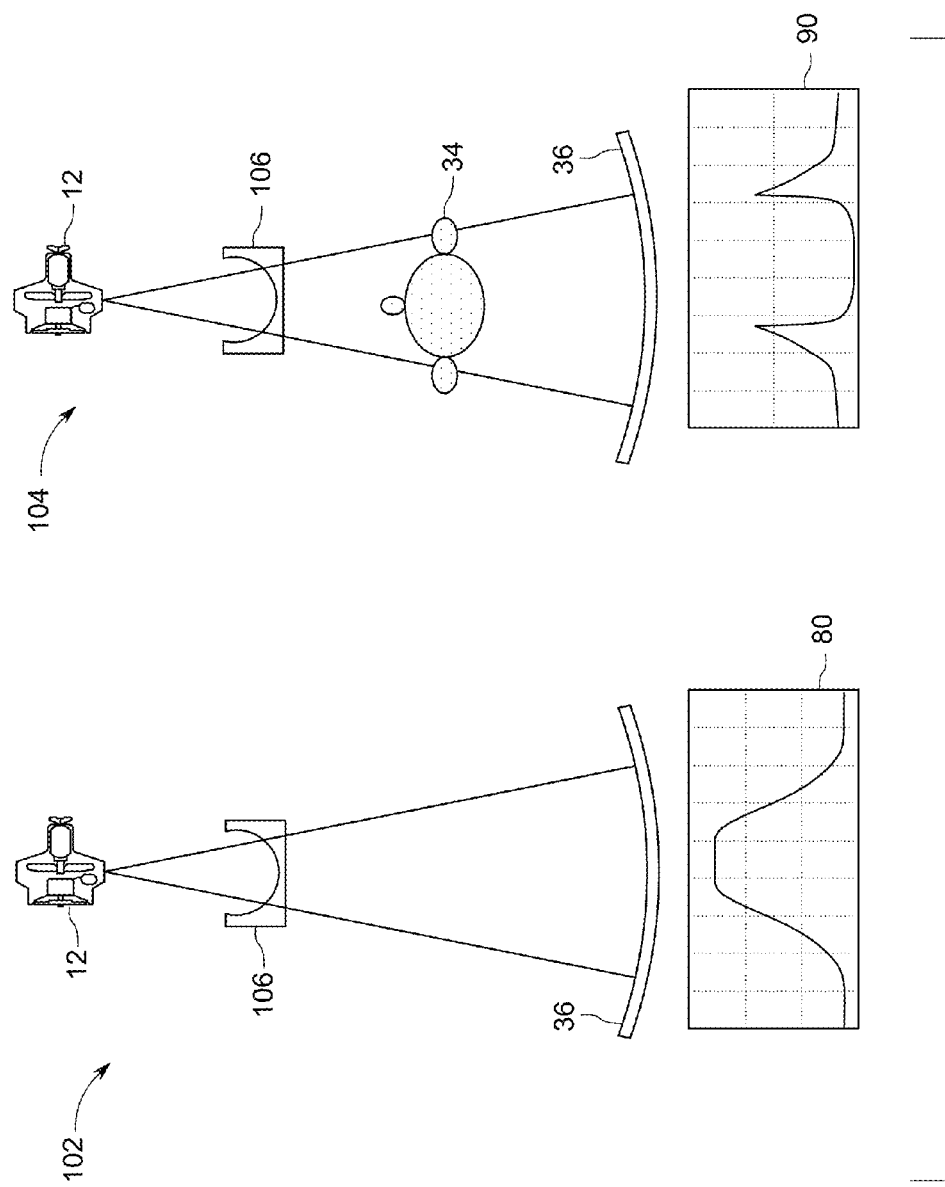
FIG. 8 is a schematic view of an embodiment of an X-ray system in a baseline scan mode and an object scan mode that may be used in conjunction with the dose estimation techniques according to an embodiment of the present disclosure.
Figure 10:
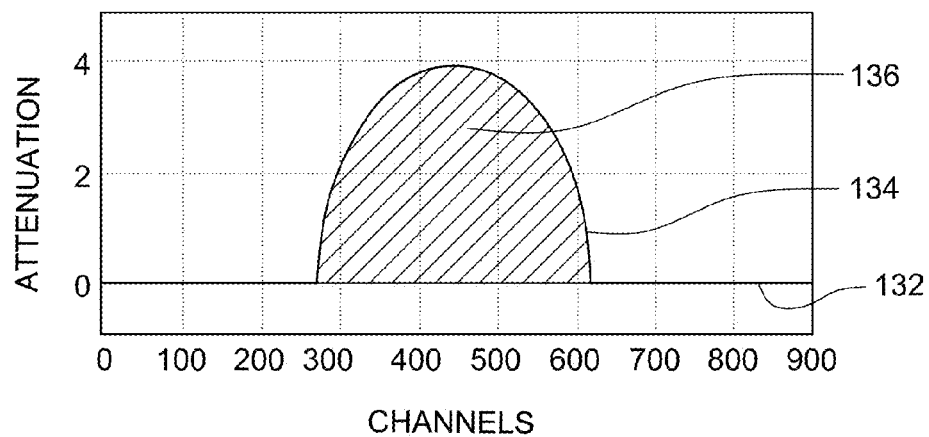
FIG. 10 is an attenuation profile that may be used to estimate object mass in conjunction with the dose estimation techniques according to an embodiment of the present disclosure.

In addition to determining an energy interaction with the object, the data from the detector 36 may also be used to estimate the object's mass. FIG. 10 is an example of a combined attenuation profile 130 generated from the preparation routines using calibration scans and an object scan. Since heavy (i.e., denser) materials generally yield high attenuation and light (i.e., less dense) materials generally yield low attenuation, the shaded area 136 under attenuation profile may be be used as the substitute to the mass of object. However, as discussed herein, the mass may be estimated through one or more other techniques, such as those provided herein. By using these two substitutes or estimates for interaction energy and mass, the dose per given view may be computed as:

$$DE_j = E_j/m_j \tag{7}$$

where $DE_j$ represents the dose estimation at view j, $E_j$ represents the interaction energy at view j or area between air and object scan intensity curves, shown in FIG. 8, and $m_j$ represents the mass contribution at view j or area below attenuation curve. $DE_j$ can be used as a rough dose metric per view since it can be computed relatively easily on the fly. Furthermore, aggregated dose metric per image slice may be also defined as $$DE = \sum_j (E_j/m_j) \tag{8}$$

where DE represent the dose estimation of the image slice corresponding to the detector row. This metric represents the dose per illuminated local region. Further, the whole body dose metric may be computed by either using real weight of the patient or using factors associated with the percentage of exposed body volume and the dose sensitivity of illuminated volume.

$$DE_{whole\ body} = (\Sigma_j E_j)/_{patient\ weight} \tag{9}$$

or $$DE_{whole\ body} = \Sigma\ \%\ \text{of exposed volume} \cdot \text{dose sensitivity} \cdot DE_{local} \tag{10}$$

In cases in which the X-ray beam has a cone geometry, this approximation may be corrected to accommodate multiple row contribution to the image slices located off from iso plane.

Figure 11:
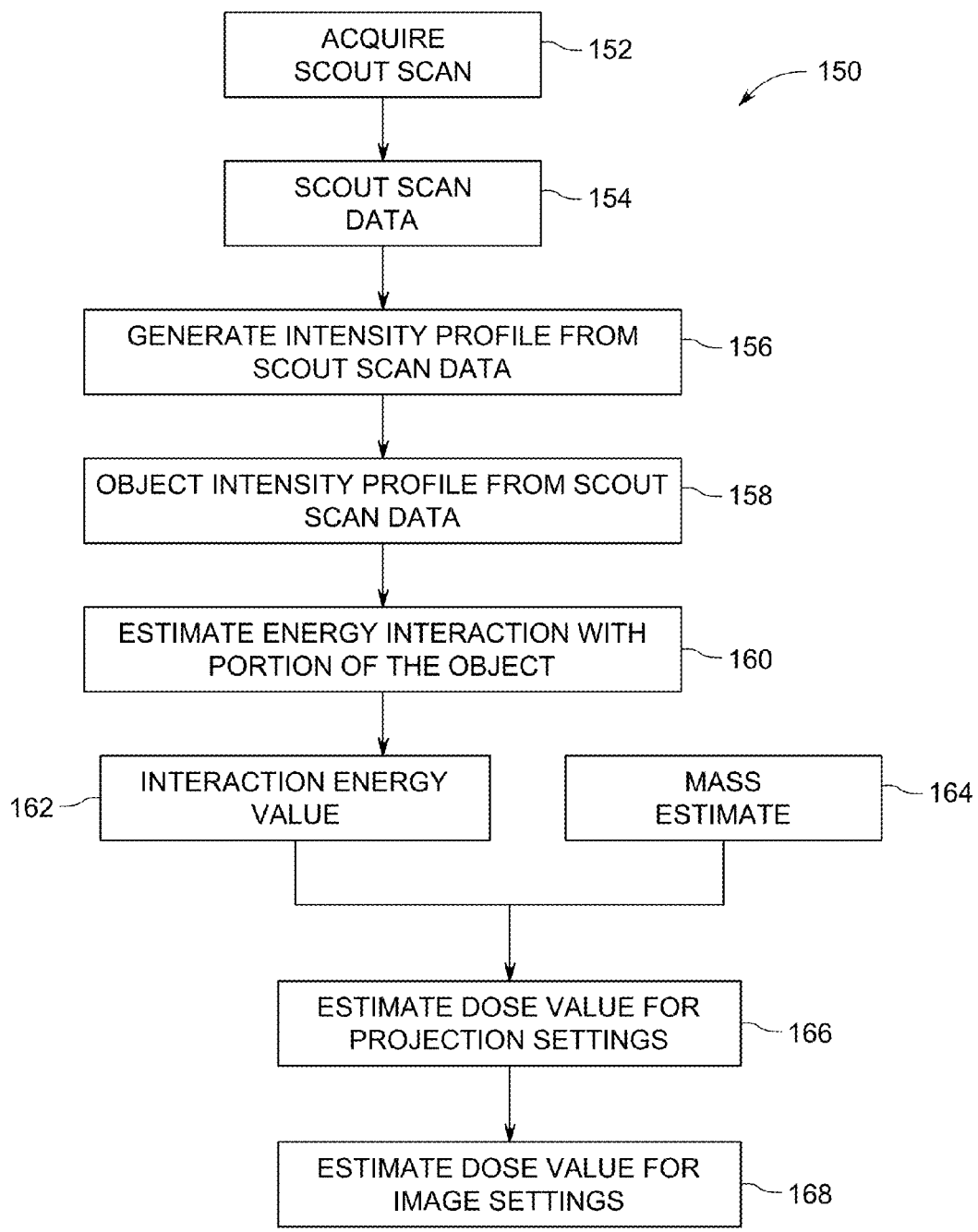
FIG. 11 is a flow diagram of an imaging dose estimation technique according to an embodiment of the present disclosure; and scout scan data provides/includes both baseline intensity profile and object intensity profile.

The disclosed X-ray dose estimation implementations may be used to estimate a CT imaging dose, as illustrated in the flow diagram of FIG. 11. The method 150 begins with acquiring a preparatory or scout image of a patient at scout settings for the CT device at block 152 to obtain scout image data 154. Further, the scout scan may be part of a full 3-D scout scan and may, in certain embodiments, involve a plurality of images and views. An object intensity profile (158) of the scout image data is generated (block 156). Based on the object intensity profile, the method 150 estimates the interaction energy in the patient for a portion of the object at block 160 to acquire an interaction energy value 162. The method 150 acquires a mass estimate at block 164, either from the scout image data 154 (as shown) or other source, and determines an estimated dose at the scout settings at block 166 to output an estimated dose value 168. To determine an estimated dose at the imaging settings at block 170, the estimated dose value 168 at the scout settings are used to extrapolate an estimated dose value at the imaging settings. For example, the data may be fitted to a line or used as variables in a transfer function that is solved for the imaging settings in question. In other embodiments, the scout image data 154 and/or the estimated dose value 168 may be matched to a closest set of modeled or empirical data (e.g., based on imaged phantoms) to estimate the imaging dose. In a specific embodiment, the empirical data may be corroborated to Monte-Carlo based results to estimate estimated imaging doses.

The estimated dose value 168 at the imaging settings may be compared to an acceptable range or threshold, either manually or automatically. A value outside of an acceptable range or threshold may trigger an alarm or may be used to exclude certain imaging settings from consideration. For example, the method 150 may be incorporated into an automatic dose-selecting feature for an X-ray device. In one embodiment, the imaging settings may be selected so that the estimated dose value 168 is within a desired range or may be optimized to a lowest possible value. In certain embodiments, the estimated dose value may be provided as an output to an operator or caregiver. For example, the estimated dose value for an imaging run may be bundled with the imaging data provided to the caregiver.

Figure 12:
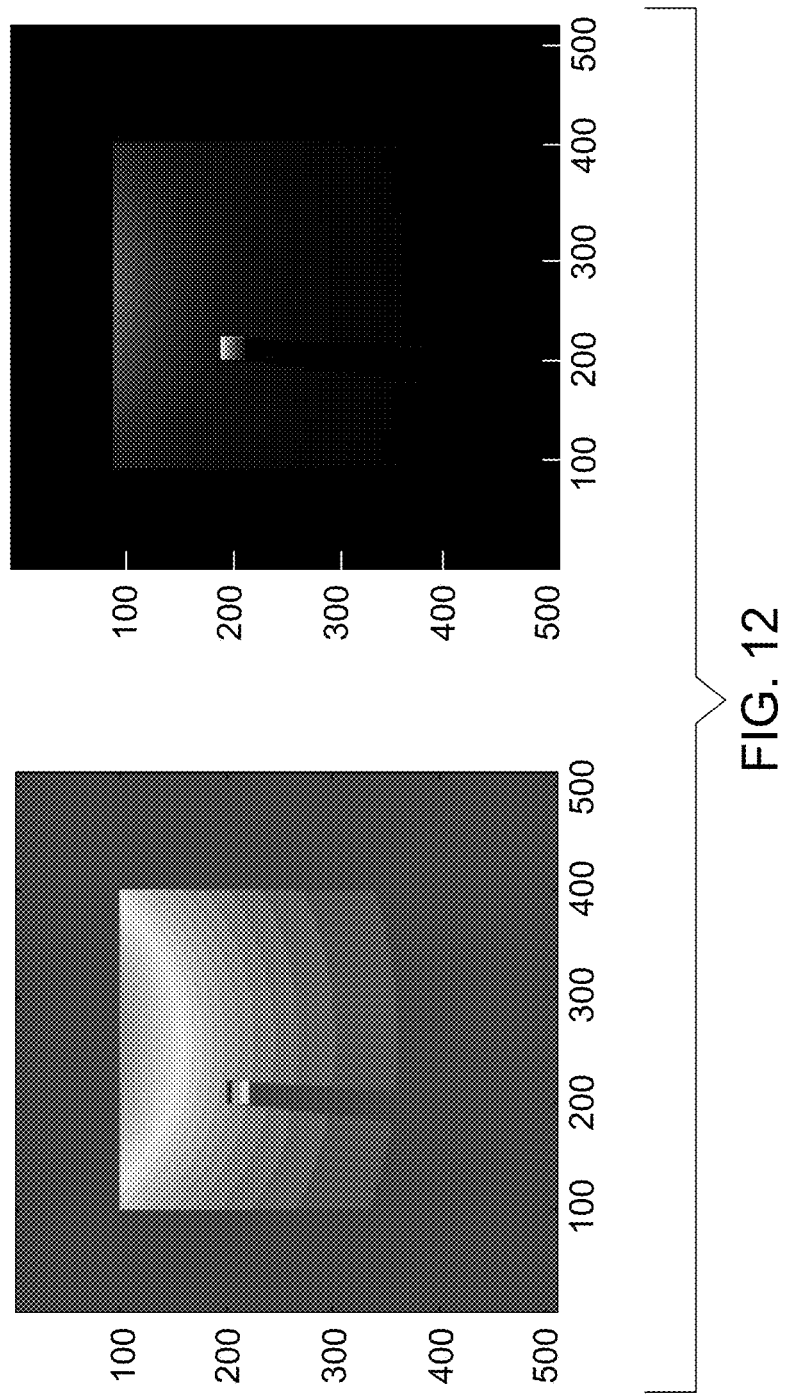
FIG. 12 is an image of a dose projection for a single view of a phantom.

FIG. 12 shows a dose back-projection for a single view for a phantom consisting of two embedded squares with different attenuation. An X-ray source location for this view is assumed at the top center for each image. As expected, the dose decreases exponentially as the x-rays propagate through the phantom and is proportional to the density. The operation may be repeated over multiple views to fully reconstruct a dose map.

The dose estimation techniques disclosed herein, because they are relatively faster than Monte Carlo-based strategies, provide the benefit of dose estimation for each patient at the time the image is acquired, i.e., the dose estimation and image acquisition may occur in a single imaging appointment for the patient. Such individualized dose estimation provides more accurate dose estimation for patients that are different sizes and have different anatomies. Further, each patient may be imaged in different areas of the body. Because different organs have different X-ray absorption profiles, doses for imaging may be determined not only on a per-patient basis, but for individual organs in the desired imaging field. Further, in certain embodiments, the dose estimation techniques may be performed without any corroboration from Monte-Carlo based strategies. That is, the dose estimation techniques may replace Monte-Carlo analysis.

In a particular embodiment, the dose estimation techniques may be used to design protocols for specific organs or anatomical structures. For example, fatty tissue is not as radiation-sensitive as reproductive organs, thyroid, bone marrow, or breast tissue. Accordingly, once a scout scan is complete, the estimated dose for the area of interest may be determined using the volumetric techniques provided herein. The settings on the device may be adjusted so that sensitive tissues receive lower doses while intervening fatty layers in the scanned object may be subjected to relatively higher doses. Further, the dose information may be used to achieve a target dose (e.g., a target average dose or a target maximum dose for any given volume or portion) for a particular organ.

This written description uses examples to disclose certain embodiments of the disclosure, including the best mode, and also to enable any person skilled in the art to practice the disclosed implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
using a processor:
receiving information generated by an X-ray detector related to detected X-rays of an X-ray beam that have passed through an object;
estimating a first energy interaction with a first portion of the object based on an intensity profile of the detected X-rays of the X-ray beam;
estimating a remaining energy in the X-ray beam after passing through the first portion of the object;
estimating a second energy interaction with a second portion of the object adjacent to the first portion of the object, wherein the X-ray beam passes through the first portion before the second portion, based on the remaining energy;
determining a first estimated dose value for the first portion based at least in part on the first energy interaction and the mass of the first portion of the object; and
determining a second estimated dose value for the second portion based at least in part on the second energy interaction and the mass of the second portion of the object.

2. The method of claim 1, comprising determining a total X-ray imaging energy for the portion of the object based on a sum including the first estimated dose value and the second estimated dose value and additional estimated dose values.

3. The method of claim 1, comprising estimating a third energy interaction with a third portion of the object based on a remaining energy of the X-ray beam after passing through the second portion of the object and determining a third estimated does value for the third portion based at least in part on the third energy interaction and the mass of the third portion of the object.

4. The method of claim 1, wherein the information generated by the X-ray detector comprises X-rays detected from a plurality of projection lines of the X-ray beam.

5. The method of claim 1, comprising determining an overlap coefficient between the X-ray beam and the first portion or the second portion.

6. The method of claim 1, wherein determining the first energy interaction comprises a sum of energy interaction for the first portion for the plurality of projection lines and determining the second energy interaction comprises a sum of energy interactions for the second portion for the plurality of projection lines.

7. The method of claim 1, comprising estimating the mass of the first portion and the second portion by estimating an average mass from a plurality of X-ray images.

8. The method of claim 1, comprising estimating the mass of the first portion and the second portion by correcting an estimated mass based on a correction factor.

9. The method of claim 1, wherein the first portion and the second portion comprise a first voxel and a second voxel adjacent to one another.

10. An X-ray system comprising:
an X-ray source configured to generate an X-ray beam through a plurality of projection lines;
a detector configured to detect X-rays of the X-ray beam that pass through an object for each respective projection line; and
a processor coupled to the detector and configured to receive information generated by the detector related to the detected X-rays, and wherein the processor is configured to execute instructions for:
dividing the object into a plurality of respective volumes;
determining an intensity profile of the detected X-rays that pass through each respective volume for each respective projection line;
determining an attenuation profile of the detected X-rays that pass through each respective volume for each respective projection line;
estimating an energy interaction for each respective volume based on the intensity profile for each respective projection line;
estimating a mass for each respective volume of the object based on at least one attenuation profile;
determining an estimated dose value for the object based at least in part on the energy interaction with each respective volume of the object for each respective projection line and the mass of each respective volume of the object.

11. The X-ray system of claim 10, wherein the estimated dose value for an individual volume comprises a sum of the respective estimated dose values for each respective projection line for the individual volume.

12. The X-ray system of claim 10, wherein the plurality of respective volumes comprise voxels.

13. The X-ray system of claim 10, wherein determining the intensity profile comprises estimating a remaining energy from the X-rays after exiting each respective volume.

14. The X-ray system of claim 10, wherein determining an estimated dose value for the object comprises summing the estimated dose values of the respective volumes of the object.

15. The X-ray system of claim 10, wherein determining an estimated dose value for the object comprises correcting each respective volume for a scatter effect across the entire object.

16. The X-ray system of claim 10, wherein determining an estimated dose value for the object comprises correcting each respective volume for a scatter effect in a voxel-dependent correction.

17. The X-ray system of claim 16, wherein the scatter effect is larger near edges of the object and wherein the correcting takes the edges into account.

18. An X-ray system, comprising:
a processor configured to receive information generated by an X-ray detector related to X-rays that have passed through an individual volume of an object, wherein the processor is configured to execute instructions for:
determining an intensity profile of the detected X-rays that pass through the volume of the object;
estimating an energy interaction with the volume of the object based on the intensity profile;
determining a remaining energy in the X-ray beam after the energy interaction; and
determining an estimated dose value for the volume of the object based at least in part on the energy interaction with the volume of the object and an estimated mass of the volume of the object.

19. The X-ray system of claim 18, comprising determining a second energy interaction for a second volume of the object based on the remaining energy.

* * * * *